US011252497B2

(12) United States Patent
Yang et al.

(10) Patent No.: US 11,252,497 B2
(45) Date of Patent: Feb. 15, 2022

(54) HEADPHONES PROVIDING FULLY NATURAL INTERFACES

(71) Applicant: Zgmicro Wuxi Corporation, Jiangsu (CN)

(72) Inventors: David Xiaodong Yang, Jiangsu (CN); Tiffany Xiao Chen, Jiangsu (CN)

(73) Assignee: Nanjing Zgmicro Company Limited, Jiangsu (CN)

( * ) Notice: Subject to any disclaimer, the term of this patent is extended or adjusted under 35 U.S.C. 154(b) by 0 days.

(21) Appl. No.: 16/988,700

(22) Filed: Aug. 9, 2020

(65) Prior Publication Data

US 2021/0099787 A1 Apr. 1, 2021

(30) Foreign Application Priority Data

Aug. 20, 2019 (CN) ........................ 201910736180.2
Aug. 20, 2019 (CN) ........................ 201910736656.2
Aug. 20, 2019 (CN) ........................ 201921295632.X

(51) Int. Cl.
*A61F 11/06* (2006.01)
*G10K 11/16* (2006.01)
*H03B 29/00* (2006.01)
*H04R 1/10* (2006.01)
*G10K 11/178* (2006.01)

(52) U.S. Cl.
CPC ..... *H04R 1/1083* (2013.01); *G10K 11/17821* (2018.01); *H04R 1/1041* (2013.01); *H04R 1/1091* (2013.01)

(58) Field of Classification Search
CPC .. H04R 1/1083; H04R 1/1041; H04R 1/1091; G10K 11/17821
See application file for complete search history.

(56) References Cited

U.S. PATENT DOCUMENTS 8,229,740 B2 * 7/2012 Nordholm ........ G10K 11/17857 704/226
10,827,249 B1 * 11/2020 Pine ..................... H04R 1/1016
2015/0066497 A1 * 3/2015 Sun ....................... G06F 16/683 704/233
2015/0371638 A1 * 12/2015 Ma .......................... G10L 15/28 704/275
2015/0373467 A1 * 12/2015 Gelter ..................... G06F 3/162 381/56

(Continued)

*Primary Examiner* — Simon King
(74) *Attorney, Agent, or Firm* — Joe Zheng

(57) ABSTRACT

Headphone providing fully natural interface are described. According to one aspect of such headphones, the headphones comprises a microphone configured for capturing an ambient sound, a speaker configured for playing audio signals, a command interface configured for receiving one or more external control commands, and a control unit having an ambient sound monitoring function. The control unit captures the ambient sound through the microphone, and automatically causes the headphones to enter an interactive mode when a preset interested sound is detected to appear in the ambient sound. The control unit controls the headphones to output an interactive reminder in the interactive mode, and the interactive reminder comprises one or more of visual reminders, a tactile reminder and an auditory reminder. Thus, interaction between the user and the ambience can be realized in a fully natural interface manner according to user preferences.

19 Claims, 2 Drawing Sheets

100

(56) References Cited

U.S. PATENT DOCUMENTS

| | | | | |
|---|---|---|---|---|
| 2016/0094927 | A1* | 3/2016 | Gooday | H04R 1/10<br>381/59 |
| 2016/0381450 | A1* | 12/2016 | Taite | G08B 3/10<br>381/74 |
| 2017/0345408 | A1* | 11/2017 | Hong | H04R 25/50 |
| 2018/0227676 | A1* | 8/2018 | Glavin | H04R 25/356 |
| 2019/0251955 | A1* | 8/2019 | Degraye | G10L 15/20 |
| 2020/0007993 | A1* | 1/2020 | Lyon | H04R 5/033 |
| 2020/0186912 | A1* | 6/2020 | Essid | H04R 1/1091 |

* cited by examiner

HEADPHONES PROVIDING FULLY NATURAL INTERFACES

BACKGROUND OF THE INVENTION

Field of the Invention

The invention relates to the field of output devices, in particular to headphones with fully natural interfaces and a method for outputting an interactive reminder.

Description of the Related Art

At present, headphones are widely used. In most cases, people use headphones to make phone calls, listen to music and so on. At present, some headphones can suppress ambient sound (noise). Some traditional wired and wireless headphones can physically eliminate ambient sounds by partially blocking the ear canals. In addition, active noise cancellation (ANC) headphones can electronically filter out ambient noises. With such ANC headphones, users cannot clearly hear the ambient noises. Therefore, these users who wear such headphones usually cannot quickly respond to key external sounds, such as a person's inquiry, alarm sound, horn sound, and etc.

The noise-cancellation headphones currently on the market try to solve the above-mentioned problems in two ways. One is to set a "Quick Reminder Mode". When the user raises his hand to cover one of the headphones, the quick reminder mode is activated. At this time, a volume of music playing on the headphones is lowered, and the external ambient sound is captured and played. The other is to set a "smart listening mode", in which an activity level of the user (i.e. walking, traveling or waiting) is detected to automatically adjust the ambient sound the user hears.

The "Quick Reminder Mode", however, requires the user to decide whether to enter this mode, and the user often fails to respond to unexpected and unnoticed interaction requests in time. For example, a male user is listening to music with the noise-canceling headphones, and his friend wants to talk to him by calling his name. Since he has not actively entered the "Quick Reminder Mode", he cannot hear his name being called by his friend, and the user would not actively enter the "Quick Reminder Mode" afterwards. It can be seen that the "Quick Reminder Mode" requires the user to activate the mode quickly, which may be viewed as a burden of starting this function on the user. The "Smart listening mode" changes the level of the ambient sound heard based on the user activity level. However, humans will not only change auditory attention based on activities in psychology. On the contrary, humans will only naturally pay attention to certain key sounds or words (such as names, siren, greetings, etc.). For example, when the headphone user is in a moving vehicle, the smart listening mode will block ambient sounds. However, the taxi driver may ask the user questions while the user is riding in the taxi. Using the "smart listening mode" of Sony's noise-canceling headphones, the user would not be able to hear the driver's voice. It can be seen that this mode is neither intuitive nor effective.

Therefore, there is a need for an improved technical solution to solve the above-mentioned problems.

SUMMARY OF THE INVENTION

One purpose of the present invention is to provide headphones with fully natural interfaces and producing an interactive reminder. The headphones allow a user to select and trigger an interaction between the user and the ambience in a fully natural interface manner according to the preferences by the user.

To achieve the purpose, according one aspect of the present invention, a headphone is provided. The headphone comprises: a microphone configured for capturing an ambient sound, a speaker configured for playing audio signals, a command interface configured for receiving one or more external control commands, and a control unit having an ambient sound monitoring function. The control unit captures the ambient sound through the microphone, and automatically triggers the headphone to enter an interactive mode when a preset interested sound appears in the ambient sound. The control unit controls the headphone to output an interactive reminder in the interactive mode, and the interactive reminder includes one type or a combination of multiple types of a visual reminder, a tactile reminder or an auditory reminder.

One of the objectives, advantages and benefits in the present invention is the mechanism of providing an interaction between a user and soundings of the user in a fully natural interface manner according to the user's needs and preferences, thereby improving convenience of interaction and making it convenient for the user to use.

There are many other objects, together with the foregoing attained in the exercise of the invention in the following description and resulting in the embodiment illustrated in the accompanying drawings.

BRIEF DESCRIPTION OF THE DRAWINGS

These and other features, aspects, and advantages of the present invention will become better understood with regard to the following description, appended claims, and accompanying drawings wherein:

DETAILED DESCRIPTION OF THE PREFERRED EMBODIMENTS

The detailed description of the invention is presented largely in terms of procedures, operations, logic blocks, processing, and other symbolic representations that directly or indirectly resemble the operations of data processing devices that may or may not be coupled to networks. These process descriptions and representations are typically used by those skilled in the art to most effectively convey the substance of their work to others skilled in the art.

Reference herein to "one embodiment" or "an embodiment" means that a particular feature, structure, or characteristic described in connection with the embodiment can be comprised in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

One purpose in the present invention is to enable a headphone or headphones with a Fully Natural Interface (or Zero User Interface) to improve the interaction between the headphones and the users thereof. By providing a user interface that is consistent with real experience or thinking model of a target user group in expected use situation, the headphones can work according to user's needs and preferences, so that the user can interact with the user interface in a most comfortable and natural way.

With reference to the above objective, a headphone with a fully natural user interface is provided according to one embodiment of the present invention. The headphone can monitor an ambient sound when a user wears the headphone to listen to music or make calls. The headphone is controlled automatically to output an interactive reminder when a predefined or preset interested sound appears in the ambient sound. The user interface is presented in fully natural way. As a result, the user would feel comfortable and it is natural to use the interface. Depending on implementation, the headphone may be a wireless headphone, such as a Bluetooth headphone, and may also be a wired headphone.

Figure 1:
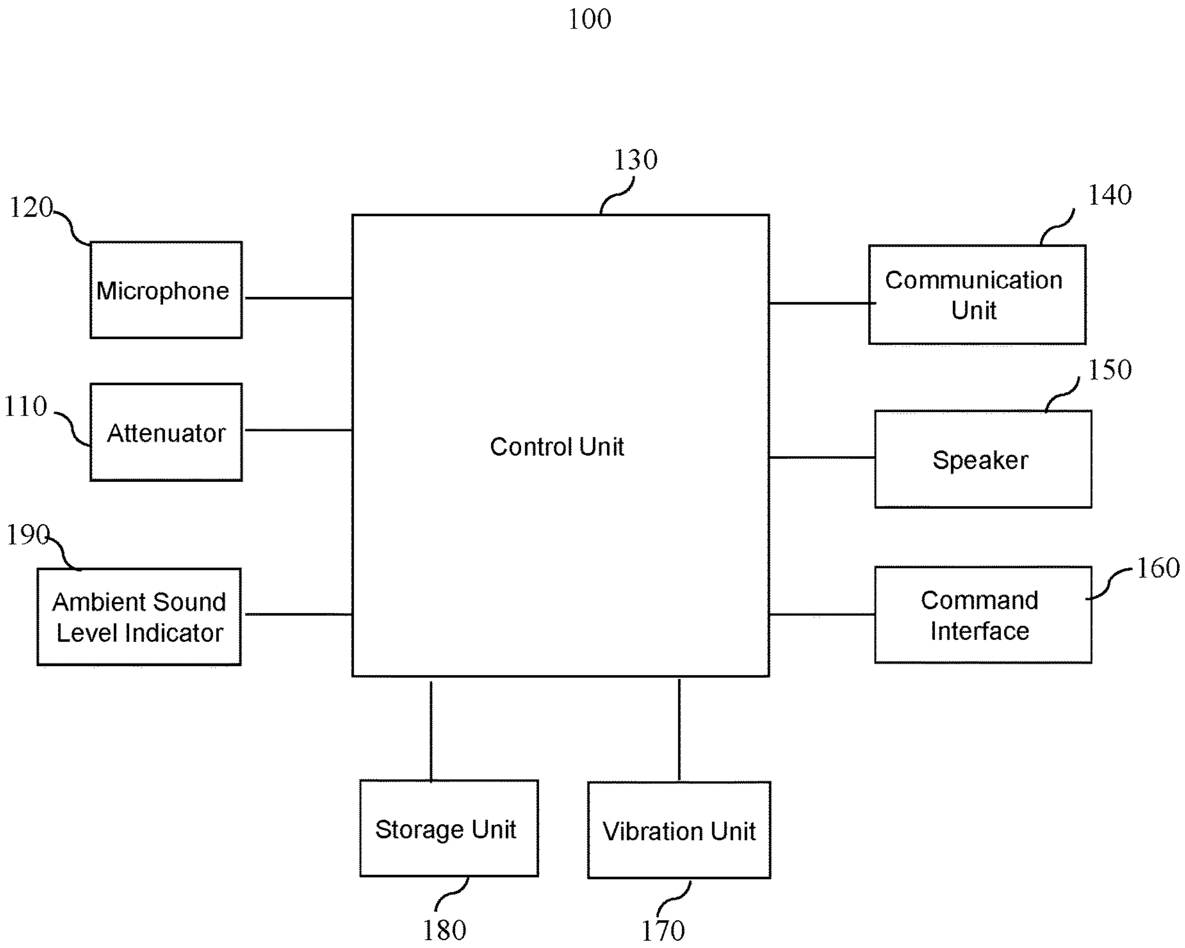
FIG. 1 is a block diagram of a headphone according to one embodiment of the present invention.

FIG. 1 is a block diagram of a headphone 100 according to one embodiment of the present invention. As shown in FIG. 1, the headphone 100 comprises an attenuator 110, a microphone 120, a control unit 130, a speaker 150, a command interface 160 and a storage unit 180. The attenuator 110, the microphone 120, the speaker 150, the command interface 160 and the storage unit 180 are all electrically coupled to the control unit 130.

The microphone 120 is configured to capture audios, mainly containing ambient sounds. Of course, the signals captured by the microphone 120 may also contain some voices of the user. The microphone 120 may be one microphone or a microphone array. The speaker 150 is configured to play audio signals. The control unit 130 is configured to control each module, and may have one or more functional modes.

In one embodiment, the headphone 100 may further comprise a communication unit 140. The communication unit 140 may comprise a wireless communication unit, and the wireless communication unit is used to establish a wireless communication connection with an external electronic device (such as a smart phone, a tablet computer, a notebook computer, a desktop computer, a vehicle communication system, etc.). The wireless communication connection transmits the audio signal from the control unit 130 to the external electronic device, and receives the audio signal from the external electronic device. The wireless communication unit may be a Bluetooth communication unit or other wireless communication units. In another embodiment, the communication unit may comprise a wired communication unit, and the wired communication unit may be used to establish a wired connection with an external electronic device (such as a smart phone, a tablet computer, a notebook computer, a desktop computer, a vehicle communication system, etc.). The wired communication connection transmits the audio signal from the control unit 130 to the external electronic device, and receives the audio signal from the external electronic device.

The storage unit 180 can store keywords, sound samples, or characteristic parameters of the sound samples that are related to the interested sound. The storage unit 180 can also store one or more types of interactive reminder. One type of interactive reminder can also be used a default interactive reminder. The storage unit 180 may also store ambient noise characteristic information. Additionally, the storage unit 180 can also be used to store other information related to the work of the headphone and user information.

The command interface 160 is configured to receive various instruction information provided by the user, including control instructions, state setting instructions, and etc. The control instruction comprises an instruction to notify the control unit 130 to enter a corresponding function mode. After receiving these instructions, the command interface 160 transmits the instruction to the control unit 130 so that the control unit 130 can enter the corresponding function mode. The state setting instructions comprise state information input entered by the user during setting up the state of the headphone, so that the headphone can perform corresponding operations according to the state information when the headphone operates.

According to one embodiment, the command interface 160 may be one or more buttons, and the control instruction is sent to the control unit 130 by triggering the button(s). According to another embodiment, the command interface 160 may also be a voice recognition interface. The user speaks a preset voice control command, and the voice recognition interface transmits the voice control command to the control unit 130.

Figure 2:
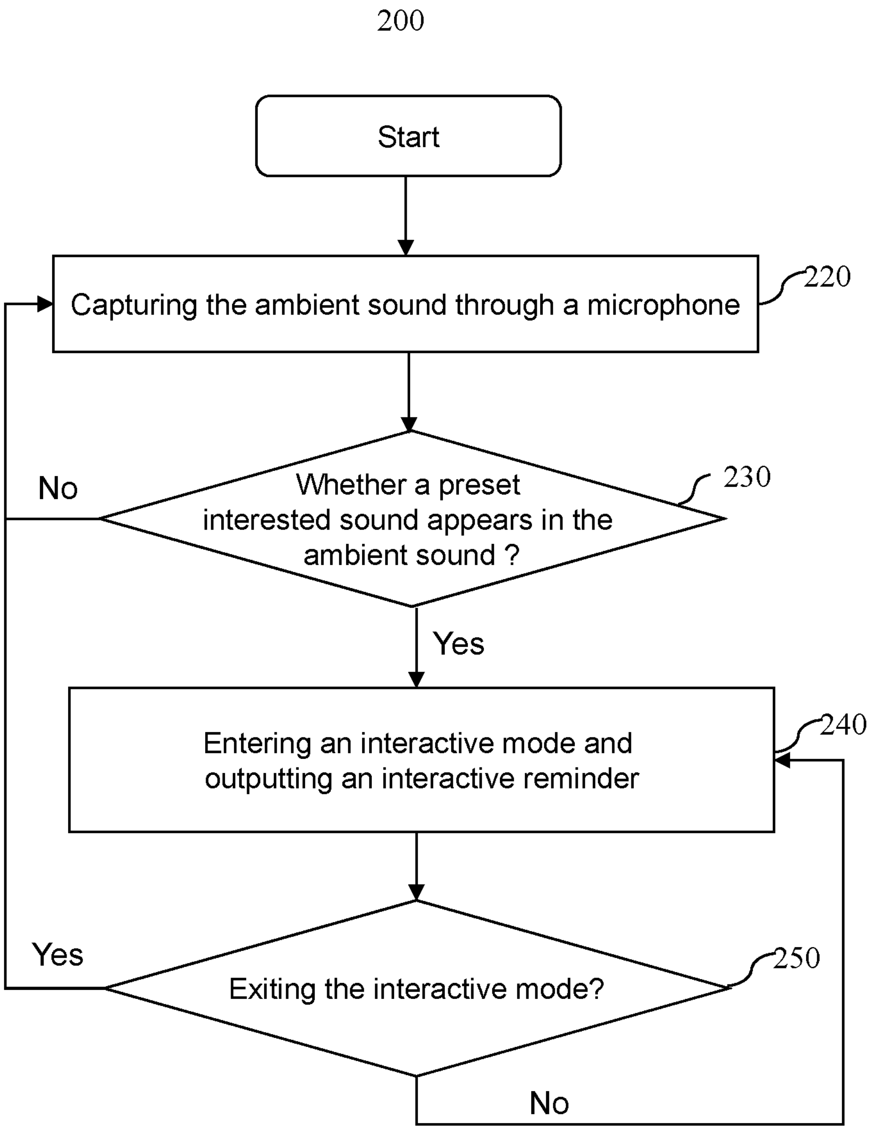
FIG. 2 is a flowchart of a method for outputting an interactive reminder according to one embodiment of the present invention.

FIG. 2 is a flowchart or process 200 of producing an interactive reminder according to one embodiment of the present invention. The process 200 may be better understood in conjunction with FIG. 1 and may be implemented in hardware, software or a combination of both hardware and software.

As shown in FIG. 2, the process 200 is started at operation 220, where the microphone 120 is activated to capture the ambient sound. The captured ambient sound can be temporarily buffered in the storage unit 180. At 230, the process 200 determines whether a preset interested sound appears in the captured ambient sound. The Yes branch leads the process 200 to operation 240, and the No branch leads the method back to operation 220 to continue capturing the ambient sound though the microphone 120.

In one embodiment, the preset interested sound may be a predetermined keyword or a predetermined voice. The predetermined keywords may be words that the user pays attention to, such as appellation (i.e. user's name, nickname, position, title, and etc.) related to an identity of the user, or commonly used start words (i.e., "hello" and "excuse me", "Sorry", etc.) during conversations. The predetermined sound may be, for example, an alarm sound, a horn sound, a door closing sound, and the like.

The interested sounds may be preset by the user. Some interested sounds, such as alarm sounds, car horns, and station announcement sounds, may also be configured before the headphone leaves the factory. In one embodiment, the headphone is used to obtain the sound samples that the user is interested in, and then the characteristic parameters of the sound samples are extracted and stored in categories. In this way, a pattern recognition algorithm can be used to detect the ambient sound captured by the microphone according to the characteristic parameters of the sound sample to determine whether the interested sound appears in the ambient sound.

At operation 240, the interactive mode is entered, and an interactive reminder is outputted in the interactive mode. Then, the process 200 goes to 250 to determine whether to exit the interactive mode. If yes, the interactive mode is exited, and the process 200 return to operation 220, where the microphone 120 continues to capture the ambient sound. If not, the process 200 returns to the operation 240, where the headphone captures the ambient sound and outputs the interactive reminders continuously. The continuous output of the interactive reminder enables users to fully receive the reminder and complete the entire interaction process in the interactive mode.

The interactive reminder comprises at least two different types of reminder. The control unit 130 selects and outputs a corresponding type of interactive reminder according to the selection of the user or perceived ambience.

In one embodiment, the interactive reminder may be an auditory reminder. The auditory reminder can have various forms. For example, the auditory reminder may be an ambient sound, that is, the ambient sound captured through the microphone 120 is played through the speaker 150 in real time as the auditory reminder, thereby helping the headphone user attend to the ambience timely and comprehensively. For another example, the auditory reminder may be a predetermined prompt sound, such as predetermined beeps, predetermined music, ring tones and etc. For another example, the auditory reminder may be an interested sound of the user. Specifically, the interested sound can be the predetermined keyword itself, the predetermined sound itself, or part or all of the ambient sound that contains the user's interested voice, or a voice dialogue containing the user's interested voice extracted from the ambient sound. For example, if the captured ambient sound is "hello, Michael, when are you going to China?" mixed with music, and the preset interested sound for is "Michael", the outputted interactive reminder can be the text or machine-simulated voice corresponding to the words "Michael", can also be the voice information "Michael" extracted from the captured ambient sound, or can also be a complete captured ambient sound including "Michael".

In addition, the interactive reminder can also be a tactile reminder. In one embodiment, a vibration unit 170 can be added to the headphone, and the vibration unit 170 can be controlled by the control unit 130 to make the headphone vibrate to realize the tactile reminder. The tactile reminder can also be realized through vibration of electronic devices such as smart phones, tablet computers, smart watches, bracelets, etc. used in conjunction with the headphone. The vibration unit 170 may be implemented by an eccentric motor or a linear vibration motor, or may be implemented by other technologies that can vibrate the device body in the future.

The interactive reminder can also be a visual reminder. For example, the visual reminder can be realized by sending a message to terminal devices such as smart phones, tablets, watches, bracelets, etc. used in conjunction with the headphone. In an application example, when a user wears the headphone to watch a movie on a tablet, the control unit 130 of the headphone may generate a message as the visual reminder if the headphone enters the interactive mode, and send the message to the tablet for display, so that the user can be reminded by showing the message on a screen of the tablet. The visual reminder may also be a light reminder, such as, setting a display screen or a button light on the headphone to flash to realize the visual reminder.

The interactive reminder can be one type of the auditory reminder, the tactile reminder, the visual reminder and other possible reminder. However, in order to provide users with natural and comfortable interactive reminders, multiple interactive reminders are outputted in the interactive mode preferably. The user can select one of the interactive reminders, or a combination of multiple types of interactive reminders according to different needs and preferences. For example, it can be a combination of the ambient sound and the tactile reminder, or a combination of predetermined ambient interactive sound and the tactile reminder, or a combination of the predetermined keyword in the user's interested sound and the visual reminder, and etc. In this way, richer ambient interactive reminders can be output. More preferably, the headphone can also automatically perceive the ambient sound, and select the most suitable interactive reminder according to the ambient sound.

In one embodiment, a certain interactive reminder in the headphone may be set as a default interactive reminder. For example, the ambient sound is set as the default interactive reminder. A plurality of types of interactive reminder is provided to allow users to select and combine the interactive reminder according to their own preferences and needs. In this way, in operation 240, whether there are user's settings in the headphone is detected. If there are no user's settings, the speaker 150 will be controlled in the interactive mode to output the default interactive reminder. If the user's setting is detected, the speaker 150, the vibration unit 170 or the communication unit 140 and other functional components can be controlled according to the user's setting to output the interactive reminder selected by the user.

In another embodiment, in order to further adapt the headphone to the requirement of the user and provide the most comfortable and natural reminder, the headphone can automatically select corresponding interactive reminder based on the ambient sound perceived by the headphone. The storage unit 180 is further configured to store ambient noise characteristic information. The control unit 130 detects the ambient sound captured by the microphone based on the ambient noise characteristic information in the interactive mode to determine a current ambient condition, and outputs the interactive reminder corresponding to the current ambient condition according to a corresponding relationship between the ambient conditions and the interactive reminders. In an application example, the headphone is pre-stored with ambient noise characteristic information such as car horn and wheel noise. When the headphone detects that there are multiple car horns and wheel noises in the current ambience, the headphone can determine that the ambience is on a road. At this time, at least car horns and human voices in the captured ambient sound can be outputted as the interactive reminder, or all the captured ambient sounds can also be outputted as the interactive reminder so that the user can pay attention to complex traffic.

In another application example, when it is detected that the noise volume of the current ambient sound is very low for a long time, or is similar to the pre-stored library noise characteristic information, it is considered that the ambience is very quiet. When the preset interested sound is detected to appear in the ambient sound, the headphone will output a soft prompt sound, such as "beep . . . " as the auditory reminder, or output a soft vibration reminder.

In one embodiment, the interactive mode may exit automatically after a certain period of time. In this embodiment, timing is started once the interactive mode is entered at the operation 240, and it is detected whether duration of the interactive mode reaches a predetermined time period. The interactive mode is exited when the predetermined time period is reached at the operation 250.

In another embodiment, the exit of the interactive mode is determined by the user. For example, the user controls the exit of the interactive mode by inputting an exit command to the headphone. At the operation 250, whether the command input by the user through the command interface 160 is an instruction to exit the interactive mode is determined. The interactive mode is exited when the exit instruction is received.

In the third embodiment, the headphone stores sound feature parameters of the user. The control unit 130 controls the microphone which may be the microphone 120, may also be another microphone closest to the user's lip to capture sound near lips of the user, detects whether the user is making a sound according to the sound feature parameters of the user, and exits the interactive mode when the user has not made a sound within a predetermined length of time at the operation 205. Compared with the above two embodiments, this way of exiting the interactive mode is more in line with design concept of fully natural user interface. The user listens to the interactive reminder in a natural way, naturally interacts with the ambience (i.e., talking to people, paying attention to the traffic, paying attention to stop information of the bus etc.), and naturally exits the interactive mode when the ambient interaction is not required. The headphone with fully natural interface is extremely comfortable and convenient to use.

In one embodiment, the process 200 may further comprise an operation of determining whether to enter the interactive mode according to a current ambient monitoring level when the preset interested sound appears in the ambient sound, and outputting corresponding interactive reminder according to the current perceived ambient monitoring level in the interactive mode. The ambient monitoring level can be used to set a state of the current ambient sound monitoring function and/or the type of the interactive reminder that can be outputted currently. The ambient monitoring level can also be used to set other working states of the headphone.

In one embodiment, the current ambient monitoring level can be determined according to the user's setting. When an ambient monitoring level preset by the user is detected, the preset ambient monitoring level is used as the current ambient monitoring level. The user can set the ambient monitoring level through the command interface 160 on the headphone, or set the ambient monitoring level on an APP on the smart phone and then transmit it to the headphone.

In another embodiment, the current ambient monitoring level can be determined according to the ambience perceived by the headphone. A current ambient condition is determined by detecting the ambient sound captured by the microphone based on the ambient noise characteristic information in the interactive mode. Then, the current ambient monitoring level is determined according to a corresponding relationship between the ambient conditions and the preset ambient monitoring level. For example, the ambient monitoring level is used to set the current state of monitoring the ambient sound, such as monitoring and non-monitoring. When the headphone perceives the ambience as a traffic environment, the ambient monitoring level is determined to be a monitoring state according to the corresponding relationship between the ambient conditions and the preset ambient monitoring level. When the headphone perceives the ambience as an extremely quiet environment, the ambient monitoring level is determined to be a non-monitoring state according to the corresponding relationship between the ambient conditions and the preset ambient monitoring level.

In one embodiment, the ambient monitoring level comprises at least two of following levels: an active attention level, a voice monitoring level, a micro-monitoring level, and a non-monitoring level. The active attention level means that the headphone is monitoring the ambient sound, and the interactive reminder being able to be outputted is that all ambient sounds captured by the microphone can be played for the user. The voice monitoring level means that the headphone is monitoring the ambient sound, and the interactive reminder being able to be outputted is that human voice captured by the microphone is played for the user. The micro-monitoring level means that the headphone is monitoring the ambient sound, and the interactive reminder being able to be outputted is that only a predetermined sound, a tactile reminder or a visual reminder is played for the user. The non-monitoring level means that the ambient sound monitoring function is closed, and no interactive reminder is outputted.

Of course, other levels of the ambient monitoring levels can be set according to specific implementation needs.

In one embodiment, when the interactive reminder is outputted in the interactive mode, the audio signal that currently needs to be played in the speaker 150 (such as the music currently being played in the speaker 150) can be paused, so as to the interactive reminder played by the speaker 150 can be clearly heard by the user. Of course, an attenuator 110 can also be used to attenuate the audio signal currently required to be played by the speaker 150 and then be played synchronously with the interactive reminder. The audio signal currently to be played can also be played through one of the left channel speaker and the right channel speaker of the speaker 150, and the interactive reminder is played through the other of the left channel speaker and the right channel speaker of the speaker 150. The audio signal can come from an external audio reproduction device (such as a mobile phone, a portable player, other headphone, or an audio equipment, etc.) that is wired or wirelessly connected to the headphone, or can come from a microphone that is mainly used to collect user voice information on the earphone device 100.

In the present invention, the microphone can selectively process the ambient sound on behalf of the headphone user, so that the user can focus on what they are doing without missing any relevant auditory clues. When the preset interested sound appears in the ambient sound, a natural and comfortable interactive reminder can be realized without user's action, thereby improving the convenience of interaction and greatly facilitating the use of the user.

In an application example, the user "Zhang San" wears the headphone 100 while walking on the road, and connects the headphone with a smart phone to listen to music. The user "Zhang San" is immersed in the music. Suddenly, a friend greeted "Zhang San" and said "Zhang San, good morning". Since the headphone 100 is monitoring the ambient sound in real time, when the keyword "Zhang San" as the preset interested sound is monitored, the headphone 100 automatically enters the interactive mode and plays the ambient sound captured by the microphone as the interactive reminder to "Zhang San". In this way, the user "Zhang San" does not need to take any actions, and can normally realize conversations with others while wearing the headphone 100. After detecting that "Zhang San" stops talking with others, the headphone will automatically exit the interactive mode. The whole use process does not require active intervention by "Zhang San", which is very convenient. At the same time, the headphone instead of "Zhang San" actively selects the ambient sounds that "Zhang San" is interested in, instead of playing all the ambient sounds. Therefore, it not only purifies the listening environment of "Zhang San", guarantees the sound quality during listening to music, but also does not miss any key ambient information. This detection and selection mechanism is completely natural because it mimics human intuitive behavior.

In another application example, the user "Zhang San" is driving while wearing the headphone 100, and suddenly an ambulance with alarm sound comes. Since the headphone 100 is monitoring the ambient sound in real time, when the alarm sound as the preset interested sound is monitored, the headphone 100 automatically enters the interactive mode. The alarm sound captured by the microphone as the interactive reminder is played until the predetermined length of time is reached or "Zhang San" manually cancel the interactive mode. Thereby, the user "Zhang San" has enough time to notice the alarm sound and take corresponding countermeasures. In this way, the user "Zhang San" can normally respond to external emergencies while wearing the headphone 100 without any action, which is very convenient.

Ambient Monitoring Level Indicator

In one embodiment, the headphone 100 further comprises an ambient monitoring level indicator 190. The ambient monitoring level indicator 190 can indicate the ambient monitoring level currently perceived by the headphone 100. The control unit 130 also determines whether to enter the interactive mode according to the currently perceived ambient monitoring level, and outputs corresponding interactive reminder according to the currently perceived ambient monitoring level in the interactive mode.

In one embodiment, the ambient monitoring level comprises one or more of an active attention level, a voice monitoring level, a micro-monitoring level, and a non-monitoring level.

The active attention level means that the headphone is monitoring the ambient sound, and the interactive reminder being able to be outputted is that all ambient sounds captured by the microphone can be played for the user. The voice monitoring level means that the headphone is monitoring the ambient sound, and the interactive reminder being able to be outputted is that only human voice captured by the microphone is played for the user. The micro-monitoring level means that the headphone is monitoring the ambient sound, and the interactive reminder being able to be outputted is that only a predetermined sound, a tactile reminder or a visual reminder is played for the user. The non-monitoring level means that the ambient sound monitoring function is closed, and no interactive reminder is outputted. In the non-monitoring level, users can be prevented from being disturbed. When the ambient monitoring level currently perceived by the headphone is the non-monitoring level, the headphone will not enter the interactive mode, and will not output the interactive reminder, since the ambient sound monitoring function of the headphone has been closed. In this way, the user can actively shield the ambient sound by setting the headphone to be the non-monitoring level, thereby avoiding being disturbed.

Of course, other ambient monitoring levels can be increased according to teaching of the present invention in other embodiment.

The user can select the ambient monitoring level of the headphone according to usage habits and scene needs. The headphone can also automatically select the current ambient monitoring level for the user according to the perceived current ambient condition. Under the design concept of the fully natural user interface, taking into account the needs of most users for natural and comfortable use, the initial ambient monitoring level of the headphone device can be set to the active attention level.

In one embodiment, the ambient monitoring level indicator 190 may be an indicator light 190. In the active attention level, the indicator light is displayed as one light effect, such as green, or blinking, etc. In the non-monitoring level, the indicator light is displayed as another light effect, such as red, or no blinking, etc. In this way, it is possible to know the ambient monitoring level which the user wearing the headphone can hear and whether a conversation is welcome by seeing the indicator light 190. Thus, a new social attribute is added on the headphone. In another embodiment, the ambient monitoring level indicator 190 can also be implemented by other specific devices. For example, the ambient monitoring level indicator may be a display screen, and the display screen displays different images according to different ambient monitoring levels.

In an application example, a user A is wearing the headphone 100 in the office, and the indicator light 190 of the headphone is green. The colleagues know that the user A welcomes the conversation after seeing the color of the indicator light 190. The colleagues can actively greet and communicate with user A. The user A can hear the voice of his friend while wearing the headphone, respond in time, and does not need to manually switch the state of the headphone. The whole process is very natural. In another application example, the user A is reading a book while wearing the headphone 100, and the indicator light 190 is red. Others know that the user A does not want to be disturbed, and may not be able to be listened after seeing the color of the indicator light 190. Thus, others can avoid disturbing user A, and user A can also avoid being disturbed by others.

The setting of the ambient monitoring level indicator 190 may even change the laws, regulations and usage habits in some regions. For example, in the law of California, the use of headphones in both ears while driving is prohibited, because people are worried that the driver will not be able to hear the warning sound of others after wearing the headphone. However, wearing the headphone in only one ear obviously greatly affects the stereo quality of the headphone and also brings discomfort to the user. Therefore, most drivers will not use the headphones. For businesses, this undoubtedly reduces the consumer group of the headphones. Using the ambient monitoring level indicator will change this situation. The driver who wear headphones in both ears can receive the ambient sounds at any time by using a unified ambient monitoring level indicator, and the police can clearly see whether the driver has used the appropriate settings (that is, the ambient sound can be heard). This may make it legal for drivers to use headphones in both ears.

Near Field Monitoring Mode and Far Field Monitoring Mode

The current headphones are basically near-field monitoring, that is, collecting the ambient sound near the headphones. On the one hand, the reason why far-field monitoring is not set is that it is difficult to implement and costly, the far-field monitoring is generally used to issue voice control commands to home appliances, and the headphones do not need remote control. On the other hand, more importantly, developers of the headphone are always accustomed to thinking that users are "immersed" in their own small world when using the headphones, and they do not need and have no time to take care of remote ambient information. Part of people's actual needs is ignored. For example, when children are listening to music in their bedroom with headphones, they also need to hear the call of their mother in the kitchen or the call of friends outside the house. It can be seen that the traditional scheme has fallen into the mindset of restricting use.

In one embodiment of the present invention, when the control unit performs the ambient sound monitoring function, a near-field monitoring mode or a far-field monitoring mode is performed according to selection of the user. The near-field monitoring mode can be performed in a default state. In the near-field monitoring mode, the microphone can be used to monitor the nearby ambient sound. In the far-field monitoring mode, the microphone can be used to monitor the remote ambient sound. In the far-field monitoring mode, if someone from a far distance (such as 5-10 meters) calls the user wearing the headphone, the headphone can still monitor the related sound, and in the near-field monitoring mode, if someone from a far distance (such as 5-10 meters) calls the user wearing the headphone, the headphone cannot monitor the related sound.

In one embodiment, the microphone 120 is a microphone array in the far-field monitoring mode. The control unit 130 controls the microphone array to collect the ambient sounds. When a sudden sound is detected in the ambient sound, the sound source is continuously picked up and recognized through sound source localization technology. Then, the control unit automatically triggers the headphone to enter the interactive mode when the preset interested sound appears in the ambient sound.

In another preferred embodiment, the microphone 120 is a microphone array in the far-field monitoring mode. The control unit 130 controls the microphone array 120 to collect the ambient sounds to obtain a plurality of ambient sound signals. The control unit 130 detects whether the interested sound appears in each ambient sound signal. When there are at least two ambient sound signals containing of the preset interested sound, the control unit automatically triggers the headphone to enter the interactive mode.

Local Privacy Mode and Remote Recognition Mode

In one embodiment, the control unit performs a local privacy protection mode or a remote recognition mode according to selection of a user when the ambient sound monitoring function is preformed. The local privacy mode can be performed in a default state. The control unit or a local electronic device detects whether the preset interested sound appears in the ambient sound according to a predetermined sound recognition algorithm in the local privacy protection mode. In the local privacy mode, there is no need to connect to the remote server through the Internet for voice recognition, which can minimize privacy leakage problems. Both Amazon's Alexa and Google Assistant are connected to the Internet, and the server performs related voice recognition. This solution has the risk of privacy leakage, because relevant information may be easily intercepted by a third party through the Internet. However, in order to provide users with convenience, the headphone of the present invention is also provided with remote recognition mode. The control unit transmits the ambient sound captured by the microphone to a remote sever through a communication unit to detect whether the preset interested sound appears in the ambient sound, and receives a detection result from the remote sever in the remote recognition mode.

Partial Playback Mode and Full Playback Mode

In a preferred embodiment, part or all of the ambient sound comprising the preset interested sound captured by the microphone may be played through the speaker according to selection of a user in the interactive mode. In the partial playback mode, only part of the sound information that contains the preset interested sound, such as the predetermined keywords or the predetermined sounds etc., in the ambient sound captured by the microphone is played through the speaker. In the full playback mode, all conversations in the ambient sound captured by the microphone can be played. For example, a friend of the headphone user said: "Hello John, How are you?" In the partial playback mode, the headphone user can only hear the keyword "Hello John". In the full playback mode, the headphone user can hear the entire conversation "Hello John, How are you?"

According to one aspect of the present invention, the present invention can be implemented as a nonvolatile computer-readable medium. The nonvolatile computer-readable medium comprises instructions executed by a processor. The instructions cause the processor to perform: capturing ambient sound; detecting the ambient sound, and triggering the headphone to enter an interactive mode when a preset interested sound appears in the ambient sound; controlling the headphone to output an interactive reminder in the interactive mode. The interactive reminder comprises one type or a combination of multiple types of a visual reminder, a tactile reminder and an auditory reminder.

Those skilled in the art should be aware that the embodiments of this application may be methods, systems, or computer program products. Accordingly, the present application may take the form of a complete hardware embodiment, a complete software embodiment, or an embodiment in conjunction with software and hardware aspects. Furthermore, the present application may take the form of a computer program product implemented on one or more computer-available storage media (including, but not limited to, disk memory, CD-ROM, optical memory, etc.) containing computer-available program code.

The present application is described with reference to methods, equipment (systems), and flow charts and/or block diagrams of computer program products according to the embodiment of the present application. It should be understood that each flow and/or block in a flowchart and/or block diagram, as well as the combination of flow and/or block in a flowchart and/or block diagram, can be implemented by computer program instructions. These computer program instructions may be provided to a processor of a general purpose computer, a dedicated computer, an embedded processor, or other programmable data processing device to produce a machine such that instructions executed by a processor of a computer or other programmable data processing device produce instructions for implementing a flow chart or more. A device for processes and/or block diagrams or functions specified in a box or multiple boxes.

These computer program instructions may also be stored in a computer-readable memory that may guide a computer or other programmable data processing device to work in a particular way, such that the instructions stored in the computer-readable memory generate a manufacturer including an instruction device that is implemented in a flow chart one or more processes. Process and/or block diagram, a box or function specified in multiple boxes.

These computer program instructions may also be loaded on a computer or other programmable data processing device such that a series of operational steps are performed on a computer or other programmable device to produce computer-implemented processing, thereby providing instructions executed on a computer or other programmable device for implementing a flow chart. The steps of a process or multiple processes and/or block diagrams, or functions specified in a box.

Although preferred embodiments of the present application have been described, additional changes and modifications to these embodiments may be made once the basic creative concepts are known to those skilled in the art. The appended claims are therefore intended to be interpreted to include preferred embodiments and all changes and modifications falling within the scope of this application.

Obviously, a person skilled in the art may make various changes and variations to the application without departing from the spirit and scope of the application. Thus, if these modifications and variations of this application fall within the scope of the claims and their equivalent technologies, the application is also intended to include these changes and variations.

We claim:

1. A headphone producing an interactive reminder, the headphone comprising:

a microphone configured to capture an ambient sound;

a speaker configured for playing audio signals;

a command interface configured for receiving one or more external control commands; and a control unit having an ambient sound monitoring function, wherein the control unit captures the ambient sound through the microphone, and causes automatically the headphone to enter an interactive mode when a preset interested sound is detected to appear in the ambient sound, the control unit controls the headphone to output an interactive reminder in the interactive mode, and the interactive reminder includes one or more of a visual reminder, a tactile reminder and an auditory reminder, the control unit is further configured to determine whether to exit the interactive mode, and control the headphone continuously to output the interactive reminder when determining that the interaction mode is not exited, the headphone stores sound feature parameters of a user, the control unit controls the microphone to capture sound near lips of the user, and detects whether the user is making a sound according to the sound feature parameters of the user, and exits the interactive mode when the user has not made a sound within a predetermined length of time.

2. The headphone according to claim 1, wherein the auditory reminder comprises one or more of an interested sound, an ambient sound, and a predetermined prompt sound, the control unit controls the speaker to output the auditory reminder, and the tactile reminder comprises a vibration reminder, the headphone comprises a vibration unit, and the control unit outputs the vibration reminder through the vibration unit; and wherein the visual reminder comprises a message reminder, the headphone further comprises a communication unit, and the control unit generates a message and sends the message through the communication unit as the message reminder.

3. The headphone according to claim 2, wherein some or all of the ambient sound comprise the preset interested sound captured by the microphone is played through the speaker according to selection of a user in the interactive mode.

4. The headphone according to claim 1, further comprising a storage unit for storing a plurality of interactive reminders, wherein the control unit controls the headphone to output one of the interactive reminders selected by a user in the interactive mode.

5. The headphone according to claim 4, wherein the storage unit is further configured to store ambient noise characteristic information, the control unit detects the ambient sound captured by the microphone based on the ambient noise characteristic information in the interactive mode to determine a current ambient condition, and outputs the interactive reminder corresponding to the current ambient condition according to a corresponding relationship between the ambient conditions and the interactive reminders.

6. The headphone according to claim 1, wherein the control unit determines whether to enter the interactive mode according to a current perceived ambient monitoring level when the preset interested sound appears in the ambient sound, and wherein the control unit controls the headphone to output a corresponding interactive reminder according to the current perceived ambient monitoring level in the interactive mode, the ambient monitoring level is used to set a state of the current ambient sound monitoring function and/or the type of the interactive reminder that can be outputted currently.

7. The headphone according to claim 6, further comprising an ambient monitoring level indicator for indicating the ambient monitoring level currently perceived by the headphone.

8. The headphone of claim 7, wherein the ambient monitoring level indicator is an indicator light or a display screen.

9. The headphone according to claim 6, wherein the ambient monitoring level comprises at least two of following levels:

an active attention level, which means that the headphone is monitoring the ambient sound, and the interactive reminder being able to be outputted is that all ambient sounds captured by the microphone can be played for the user;

a voice monitoring level, which means that the headphone is monitoring the ambient sound, and the interactive reminder being able to be outputted is that only human voice captured by the microphone is played for the user;

a micro-monitoring level, which means that the headphone is monitoring the ambient sound, and the interactive reminder being able to be outputted is that a predetermined sound, a tactile reminder or a visual reminder is played for the user; and a non-monitoring level, which means that the ambient sound monitoring function is closed, and no interactive reminder is outputted.

10. The headphone according to claim 1, wherein a near-field monitoring mode or a far-field monitoring mode is preformed according to a selection from a user when the control unit performs the ambient sound monitoring function, the microphone can be used to monitor the nearby ambient sound in the near-field monitoring mode, and the microphone can be used to monitor the remote ambient sound in the far-field monitoring mode.

11. The headphone according to claim 1, wherein the control unit performs a local privacy protection mode or a remote recognition mode according to a selection of a user when the ambient sound monitoring function is preformed, the control unit or a local electronic device detects whether the preset interested sound appears in the ambient sound according to a predetermined sound recognition algorithm in the local privacy protection mode; and the control unit transmits the ambient sound captured by the microphone to a remote sever through a communication unit to detect whether the preset interested sound appears in the ambient sound, and receives a detection result from the remote sever in the remote recognition mode.

12. A method for a headphone to headphone producing an interactive reminder, the method comprising:

capturing an ambient sound by a microphone in a headphone;

detecting the ambient sound, and triggering the headphone to enter an interactive mode when a preset interested sound is detected to appear in the ambient sound;

determining whether to enter the interactive mode according to a current ambient monitoring level before causing the headphone to enter the interactive mode, wherein the ambient monitoring level comprises at least two of:

an active attention level indicating the headphone is monitoring the ambient sound, and all ambient sounds captured by the microphone are played for the user when the user chooses to do so;

a voice monitoring level indicating that the headphone is monitoring the ambient sound, and only human voice captured by the microphone is played for the user;

a micro-monitoring level indicating that the headphone is monitoring the ambient sound, and only a predetermined sound, a tactile reminder or visual reminder is played for the user;

a non-monitoring level indicating that the ambient sound monitoring function is closed, and no interactive reminder is outputted;

outputting a corresponding interactive reminder according to the current perceived ambient monitoring level in the interactive mode after entering the interactive mode, wherein the ambient monitoring level is used to set a state of the current ambient sound monitoring function and/or the type of the interactive reminder that can be outputted currently; and controlling the headphone to produce an interactive reminder in the interactive mode, wherein the interactive reminder comprises one type or a combination of multiple types of a visual reminder, a tactile reminder and an auditory reminder.

13. The method according to claim 12, wherein the auditory reminder comprises one or more of an interested sound, an ambient sound and a predetermined prompt sound, the tactile reminder comprises a vibration reminder, and the visual reminder comprises a message reminder and/or light reminder.

14. The method according to claim 12, wherein when a preset ambient monitoring level is detected, the preset ambient monitoring level is used as a current ambient monitoring level; or the ambient sound captured by the microphone is detected based on ambient noise characteristic information in the interactive mode to determine a current ambient condition, and the current ambient monitoring level is determined according to a corresponding relationship between the ambient conditions and the preset ambient monitoring level.

15. The method according to claim 12, further comprising indicating the ambient monitoring level currently perceived by an ambient monitoring level indicator.

16. The method according to claim 12, further comprising:

presetting ambient noise characteristic information;

detecting the ambient sound captured by the microphone based on the ambient noise characteristic information in the interactive mode to determine a current ambient condition, and outputting the interactive reminder corresponding to the current ambient condition according to a corresponding relationship between the ambient conditions and the interactive reminders.

17. The method according to claim 12, wherein the ambient sound in the auditory reminder comprises part or all of the ambient sound captured by the microphone and containing the preset interested sound; or the ambient sound in the auditory reminder is part or all of the ambient sound captured by the microphone.

18. The method according to claim 12, wherein a near-field monitoring mode or a far-field monitoring mode is performed according to selection of a user in the interactive mode.

19. The method according to claim 12, wherein a local privacy protection mode or a remote recognition mode is performed to detect whether the preset interested sound appears in the ambient sound according to selection of a user, whether the preset interested sound appears in the ambient sound is detected according to a predetermined sound recognition algorithm in a local device in the local privacy protection mode; and the ambient sound captured by the microphone is transmitted to a remote sever to detect whether the preset interested sound appears in the ambient sound, and a detection result from the remote sever is received in the remote recognition mode.

* * * * *